United States Patent
Gutman et al.

(10) Patent No.: US 7,227,021 B2
(45) Date of Patent: Jun. 5, 2007

(54) PROCESS FOR PREPARING 1-METHOXYMETHYL-5,5-DIPHENYL BARBITURIC ACID

(75) Inventors: Daniella Gutman, Rishon Lezion (IL); Rosa Cyjon, Haifa (IL)

(73) Assignee: Tara Pharmaceutical Industries Ltd, Haifa Bay (IL)

( * ) Notice: Subject to any disclaimer, the term of this patent is extended or adjusted under 35 U.S.C. 154(b) by 0 days.

(21) Appl. No.: 11/380,066

(22) Filed: Apr. 25, 2006

(65) Prior Publication Data

US 2006/0258864 A1 Nov. 16, 2006

Related U.S. Application Data

(63) Continuation of application No. 11/173,499, filed on Jul. 1, 2005, now Pat. No. 7,064,205.

(60) Provisional application No. 60/584,955, filed on Jul. 2, 2004.

(51) Int. Cl.
*C07D 239/62* (2006.01)
*C07D 239/66* (2006.01)

(52) U.S. Cl. ...................................... 544/299; 544/302

(58) Field of Classification Search ................ 544/299, 544/302
See application file for complete search history.

(56) References Cited

U.S. PATENT DOCUMENTS

| 4,029,662 | A | 6/1977 | Vida |
| 4,628,056 | A | 12/1986 | Levitt et al. |
| 6,093,820 | A | 7/2000 | Gutman et al. |
| 7,064,205 | B2 * | 6/2006 | Gutman et al. ............. 544/299 |

OTHER PUBLICATIONS

McElvain, S.M. "5-5 Diphenyl Barbituric Acid" (J. Am. Chem. Soc.) Jul.-Dec. 1935, 57: 1303-1304.
Barnes, Harry M. and McElvain, S.M. "For further observations on the Condensation of Benzene with Alloxan" (J. Am. Chem. Soc.) Jul.-Dec. 1937, 59: 2348-2351.
Boron Tribromide, Encyclopedia of Reagents for Organic Synthesis edited by Leo Pacquette, pp. 1-9, 2003.

* cited by examiner

*Primary Examiner*—Venkataraman Balasubramanian

(57) ABSTRACT

The present invention provides a novel process for preparing 1-methoxymethyl-5,5-diphenylbarbituric acid. In particular, the present invention provides a process for preparing 1-methoxymethyl-5,5-diphenylbarbituric acid by reacting 1,3-bis(methoxymethyl)-5,5-diphenylbarbituric acid with a Lewis acid to selectively remove one methoxymethyl group from 1,3-bis(methoxymethyl)-5,5-diphenylbarbituric acid.

9 Claims, No Drawings

PROCESS FOR PREPARING 1-METHOXYMETHYL-5,5-DIPHENYLBARBITURIC ACID

CROSS REFERENCE TO RELATED APPLICATION

This application is a continuation of U.S. Utility application Ser. No. 11/173,499 filed Jul. 1, 2005, now U.S. Pat. No. 7,064,205, which claims the benefit under 35 U.S.C. § 119(e) of U.S. Provisional Application No. 60/584,955, filed July 2, 2004, the disclosure of which is hereby incorporated by reference in its entirety herein.

FIELD OF THE INVENTION

The present invention relates to a process for preparing 1-methoxymethyl-5,5-diphenylbarbituric acid. In particular, the present invention relates to a process for preparing 1-methoxymethyl-5,5-diphenylbarbituric acid by reacting 1,3-bis(methoxymethyl)-5,5-diphenylbarbituric acid with a Lewis acid to selectively remove one methoxymethyl group from 1,3-bis(methoxymethyl)-5,5-diphenylbarbituric acid.

BACKGROUND OF THE INVENTION

Barbituric acid (CAS # 67-52-7, CAS name: 2,4,6(1H, 3H,5H)-pyrimidinetrione) and its derivatives possess useful pharmacological properties, including anti-convulsant, anti-anxiety and muscle-relaxant activities. In addition, many barbituric acid derivatives further possess sedative and/or hypnotic activities, which makes the compounds disadvantageous for patients who wish to maintain mental acuity.

1,3-bis(methoxymethyl)-5,5-diphenylbarbituric acid is a barbituric acid derivative that possesses anti-convulsant, anti-anxiety and muscle-relaxant activities, but does not possess major sedative or hypnotic activities. As such, the compound is considered to be a promising candidate for patients who wish to maintain mental acuity.

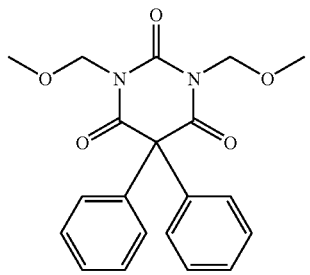

1, 3-bis (methoxymethl)-5, 5-diphenylbarbituric acid

U.S. Pat. No. 4,628,056 (the '056 patent) discloses a process for preparing 1,3-bis(methoxymethyl)-5,5-diphenylbarbituric acid, wherein 5,5-diphenylbarbituric acid is reacted with sodium hydride and chloromethyl methyl ether. The reaction results in the addition of two methoxymethyl groups to the 5,5-diphenylbarbituric acid to form 1,3-bis (methoxymethyl)-5,5-diphenylbarbituric acid.

1-methoxymethyl-5,5-diphenylbarbituric acid is an analog of 1,3-bis(methoxymethyl)-5,5-diphenylbarbituric acid that is believed to possess a similar spectrum of activity. Thus, 1-methoxymethyl-5,5-diphenylbarbituric acid is believed to possess anti-convulsant, anti-anxiety and muscle-relaxant activities, without possessing major sedative or hypnotic activities, and is similarly considered to be a promising candidate for patients who wish to maintain mental acuity.

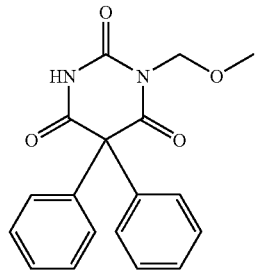

1-methoxymethyl-5, 5-diphenylbarbituric acid

U.S. Pat. No. 6,093,820 discloses a two step process for preparing 1-methoxymethyl-5,5-diphenylbarbituric acid, in which 5,5-diphenylbarbituric acid is first reacted with excess sodium hydride, and then reacted with methoxymethyl methanesulfonate. As in the '056 patent, the '820 patent process utilizes 5,5-diphenylbarbituric acid as a starting material, but only one methoxymethyl group is added, not two. The '820 patent further discloses a pharmaceutical formulation of 1-methoxymethyl-5,5-diphenylbarbituric acid for treating convulsions, seizures, muscle stiffness, nervous strain and anxiety.

There is a continuing need for a process for preparing 1-methoxymethyl-5,5-diphenylbarbituric acid.

SUMMARY OF THE INVENTION

The present invention provides a process for preparing 1-methoxymethyl-5,5-diphenylbarbituric acid comprising the steps of:

(a) reacting 1,3-bis(methoxymethyl)-5,5-diphenylbarbituric acid with about 0.2 to about 2 equivalents of a Lewis acid selected from the group consisting of aluminum chloride, boron trifluoride diethyl etherate, boron tribromide, and mixtures thereof, at a temperature of about 70° C. to about 130° C., for about one to about five hours; and (b) isolating the 1-methoxymethyl-5,5-diphenylbarbituric acid.

Preferably, the Lewis acid is aluminum chloride.

Preferably, step (a) is performed in an aromatic solvent. More preferably, the aromatic solvent is selected from the group consisting of chlorobenzene, bromobenzene, nitrobenzene, dichlorobenzene, o-nitrotoluene, anisole, and mixtures thereof. More preferably, the aromatic solvent is chlorobenzene.

Preferably, the 1,3-bis(methoxymethyl)-5,5-diphenylbarbituric acid is reacted with about 0.4 to about 1 equivalent of the Lewis acid. More preferably, the 1,3-bis(methoxymethyl)-5,5-diphenylbarbituric acid is reacted with about 0.6 equivalent of the Lewis acid.

Preferably, step (a) is performed at a temperature of about 80° C. to about 120° C. More preferably, step (a) is performed at a temperature of about 90° C. to about 110° C.

Preferably, step (a) is performed for about two hours.

Preferably, the 1-methoxymethyl-5,5-diphenylbarbituric acid is produced as a single batch of at least about 500 grams.

Preferably, step (b) further comprises the steps of:
a') extracting the 1-methoxymethyl-5,5-diphenylbarbituric acid into a basic aqueous solution;
b') acidifying the basic aqueous solution to precipitate the extracted 1-methoxymethyl-5,5-diphenylbarbituric acid; and
c') collecting the precipitated 1-methoxymethyl-5,5-diphenylbarbituric acid.

Preferably, the basic aqueous solution is a sodium hydroxide solution.

Preferably, when step (a) is performed in an aromatic solvent, step (b) further comprises the steps of:
a') combining the aromatic solvent with water to form a precipitate;
b') separating the aromatic solvent from the water and the precipitate;
c') extracting the 1-methoxymethyl-5,5-diphenylbarbituric acid from the aromatic solvent into a basic aqueous solution;
d') acidifying the basic aqueous solution to precipitate the extracted 1-methoxymethyl-5,5-diphenylbarbituric acid; and
e') collecting the precipitated 1-methoxymethyl-5,5-diphenylbarbituric acid.

Preferably, the basic aqueous solution is a sodium hydroxide solution.

Preferably, when step (a) is performed in an aromatic solvent, step (b) further comprises the steps of:
a') combining the aromatic solvent with an acidic aqueous solution to form a precipitate;
b') separating the aromatic solvent from the acidic aqueous solution and the precipitate;
c') evaporating the aromatic solvent to form a concentrate;
d') dissolving the concentrate in a non-aromatic organic solvent;
e') extracting the 1-methoxymethyl-5,5-diphenylbarbituric acid from the non-aromatic organic solvent into a basic aqueous solution;
f') acidifying the basic aqueous solution to precipitate the extracted 1-methoxymethyl-5,5-diphenylbarbituric acid; and
g') collecting the precipitated 1-methoxymethyl-5,5-diphenylbarbituric acid.

Preferably, the basic aqueous solution is a sodium hydroxide solution.

Preferably, the non-aromatic organic solvent is selected from the group consisting of ethyl acetate, diethyl ether, methylene chloride, and mixtures thereof. More preferably, the non-aromatic organic solvent is ethyl acetate.

Preferably, the process further comprises the step of purifying the isolated 1-methoxymethyl-5,5-diphenylbarbituric acid. Preferably, the purifying step is performed by crystallization from a solvent. Preferably, the solvent is at least one solvent selected from the group consisting of toluene, tert-butyl methyl ether, ethanol, methanol, water mixed with ethanol, and water mixed with methanol.

Preferably, the 1-methoxymethyl-5,5-diphenylbarbituric acid has a purity greater than 99%.

DETAILED DESCRIPTION OF THE INVENTION

As used herein, the following terms are defined: "Lewis acid" refers to any species that can accept a pair of electrons and form a coordinate covalent bond; "equivalent" refers to the relative molar quantity (i.e., mole/mole ratio) of one reagent in a chemical reaction with reference to another; "aromatic solvent" refers to a solvent having a molecular structure that includes a phenyl ring; "non-aromatic organic solvent" refers to an organic solvent having a molecular structure that does not include a phenyl ring; "isolating 1-methoxymethyl-5,5-diphenylbarbituric acid" refers to separating 1-methoxymethyl-5,5-diphenylbarbituric acid into a composition of matter, wherein the fraction (by weight) of the 1-methoxymethyl-5,5-diphenylbarbituric acid in the composition is greater than the fraction (by weight) of each other component of the composition, taken individually; "basic aqueous solution" refers to an aqueous solution, optionally including a water miscible organic solvent (e.g., methanol), having a pH greater than 7; an "acidic aqueous solution" refers to an aqueous solution, optionally including a water miscible organic solvent (e.g., methanol), having a pH less than 7; "commercial scale" refers to a batch size of at least about 100 grams; "batch" refers to the quantity of a product formed during a single chemical process.

The present invention provides a process for preparing 1-methoxymethyl-5,5-diphenylbarbituric acid comprising the steps of:
(a) reacting 1,3-bis(methoxymethyl)-5,5-diphenylbarbituric acid with about 0.2 to about 2 equivalents of a Lewis acid selected from the group consisting of aluminum chloride, boron trifluoride diethyl etherate, boron tribromide, and mixtures thereof, at a temperature of about 70° C. to about 130° C., for about one to about five hours; and
(b) isolating the 1-methoxymethyl-5,5-diphenylbarbituric acid.

Suitable processes for preparing 1,3-bis(methoxymethyl)-5,5-diphenylbarbituric acid are known in the art. For example, 1,3-bis(methoxymethyl)-5,5-diphenylbarbituric acid may be prepared by the following two steps: (1) reacting dimethoxymethane with acetyl methanesulfonate; and (2) reacting the resulting methoxymethyl methanesulfonate with 5,5-diphenylbarbituric acid in the presence of N,N-diisopropylethylamine. This two-step process is described in detail in U.S. Pat. No. 6,093,820, which is incorporated herein by reference in its entirety.

The 5,5-diphenylbarbituric acid used in step (2) of the above process may be prepared by reacting benzene with alloxan as described by S. M. McElvain in "5,5-diphenylbarbituric acid," *J. Am. Chem. Soc.* 1935, 57, 1303–1304. See also Barnes, H. M. and McElvain, S. M., "Further observations on the condensation of benzene with alloxan," *J. Am. Chem. Soc.* 1937, 59, 2348–2351. The McElvain and Barnes and McElvain articles are incorporated herein by reference in their entireties.

The 1,3-bis(methoxymethyl)-5,5-diphenylbarbituric acid used in step (a) of the present process may be crystalline, amorphous, semisolid, syrup, a mixture thereof, or the like. Crystalline 1,3-bis(methoxymethyl)-5,5-diphenylbarbituric acid may include polymorphs, solvates, clathrates, and the like, and mixtures thereof.

Optionally, the 1,3-bis methoxymethyl)-5,5-diphenylbarbituric acid used in step (a) of the present invention may be crude. Crude 1,3-bis(methoxymethyl)-5,5-diphenylbarbituric acid refers to 1,3-bis(methoxymethyl)-5,5-diphenylbarbituric acid that is synthesized by a chemical reaction and isolated from the reaction mixture, but not further purified.

The Lewis acid is selected from the group consisting of aluminum chloride, boron trifluoride diethyl etherate, boron tribromide, and mixtures thereof. Preferably, the Lewis acid is aluminum chloride.

Optionally, the reacting step (a) may be performed in a solvent. Suitable solvents include, but are not limited to, aromatic solvents. Suitable aromatic solvents include, but are not limited to, chlorobenzene, bromobenzene, nitrobenzene, dichlorobenzene, o-nitrotoluene, anisole, mixtures thereof, and the like. Preferably, the aromatic solvent is chlorobenzene.

The reaction conditions (e.g., reagent ratio, reaction temperature, reaction time) in step (a) may be suitably controlled to ensure that the Lewis acid selectively removes one methoxymethyl group from 1,3-bis(methoxymethyl)-5,5-diphenylbarbituric acid to form 1-methoxymethyl-5,5-diphenylbarbituric acid. With reference to the reagent ratio, reacting step (a) is performed using about 0.2 to about 2 equivalents of the Lewis acid (i.e., the mole/mole ratio of the Lewis acid to the 1,3-bis(methoxymethyl)-5,5-diphenylbarbituric acid is about 0.2 to about 2). Preferably, step (a) is performed using about 0.4 to about 1 equivalent of the Lewis acid. More preferably, step (a) is performed using about 0.6 equivalent of the Lewis acid.

With reference to reaction temperature, step (a) is performed at a temperature of about 70° C. to about 130° C. Preferably, step (a) is performed at a temperature of about 80° C. to about 120° C. More preferably, step (a) is performed at a temperature of about 90° C. to about 110° C.

With reference to reaction time, step (a) is performed for about one (1) to about five (5) hours. Preferably, step (a) is performed for about two (2) hours.

In a preferred embodiment, the process of the present invention is performed at a commercial scale. Preferably, the 1-methoxymethyl-5,5-diphenylbarbituric acid is produced as a single batch of at least about 100 grams. More preferably, the 1-methoxymethyl-5,5-diphenylbarbituric acid is produced as a single batch of at least about 500 grams. More preferably, the 1-methoxymethyl-5,5-diphenylbarbituric acid is produced as a single batch of at least about one (1) kilogram.

In accordance with the present invention, the prepared 1-methoxymethyl-5,5-diphenylbarbituric acid may be isolated in step (b) using standard methods. Suitable isolation methods include, but are not limited to, removing the solvent from the reaction mixture. Suitable isolation methods further include, but are not limited to, the following three embodiments.

In a first embodiment, the isolating step (b) may further comprise the steps of:
a') extracting the 1-methoxymethyl-5,5-diphenylbarbituric acid into a basic aqueous solution;
b') acidifying the basic aqueous solution to precipitate the extracted 1-methoxymethyl-5,5-diphenylbarbituric acid; and
c') collecting the precipitated 1-methoxymethyl-5,5-diphenylbarbituric acid.

In a second embodiment, the reacting step (a) may be performed in an aromatic solvent, and the isolating step (b) may further comprise the steps of:
a') combining the aromatic solvent with water to form a precipitate;
b') separating the aromatic solvent from the water and the precipitate;
c') extracting the 1-methoxymethyl-5,5-diphenylbarbituric acid from the aromatic solvent into a basic aqueous solution;
d') acidifying the basic aqueous solution to precipitate the extracted 1-methoxymethyl-5,5-diphenylbarbituric acid; and
e') collecting the precipitated 1-methoxymethyl-5,5-diphenylbarbituric acid In a third embodiment, the reacting step (a) may be performed in an aromatic solvent, and the isolating step (b) may further comprise the steps of:
a') combining the aromatic solvent with an acidic aqueous solution to form a precipitate;
b') separating the aromatic solvent from the acidic aqueous solution and the precipitate;
c') evaporating the aromatic solvent to form a concentrate;
d') dissolving the concentrate in a non-aromatic organic solvent;
e') extracting the 1-methoxymethyl-5,5-diphenylbarbituric acid from the non-aromatic organic solvent into a basic aqueous solution;
f') acidifying the basic aqueous solution to precipitate the extracted 1-methoxymethyl-5,5-diphenylbarbituric acid; and
g') collecting the precipitated 1-methoxymethyl-5,5-diphenylbarbituric acid.

The second and third of the above-described embodiments each begins with two steps: a combining step, followed by a separating step.

With reference to the combining step, in the second embodiment the combining step a') is performed by adding water to the aromatic solvent in a quantity sufficient to cause a precipitate to form. Preferably, the combining step is performed using a vol/vol ratio of the water to the aromatic solvent of about 0.1:1 to about 2:1. More preferably, the combining step is performed using a vol/vol ratio of the water to the aromatic solvent of about 0.3:1 to about 1:1. More preferably, the combining step is performed using a vol/vol ratio of the water to the aromatic solvent of about 0.5:1.

In the third embodiment, the combining step a') is performed by adding an acidic aqueous solution to the aromatic solvent in a quantity sufficient to cause a precipitate to form. The acidic aqueous solution may be prepared using standard methods. Suitable methods include, but are not limited to, dissolving an acid in water, and dissolving an acid in a mixture of water and one or more water miscible organic solvents. Suitable acids include, but are not limited to, mineral acids. Suitable water miscible organic solvents include, but are not limited to, methanol.

With reference to the separating step, in the second embodiment the separating step b') is performed by removing the precipitate and the water from the aromatic solvent. In the third embodiment, the separating step b') is performed by removing the precipitate and the acidic aqueous solution from the aromatic solvent. Suitable methods for removing the precipitate from the aromatic solvent include, but are not limited to, filtering, centrifuging, and decanting. Suitable methods for removing the water or the acidic aqueous solution from the aromatic solvent include, but are not limited to, using a separatory funnel.

The third of the above-described embodiments includes two intermediate steps: an evaporating step; followed by a dissolving step.

The evaporating step c') is performed by evaporating a portion of the separated aromatic solvent to form a concentrate, which contains 1-methoxymethyl-5,5-diphenylbarbituric acid. The evaporating step may be performed using any suitable method. Suitable methods include, but are not limited to, heating the aromatic solvent to an elevated temperature, and exposing the aromatic solvent to a reduced pressure. Preferably, the evaporating step is performed until substantially all of the aromatic solvent is evaporated.

The dissolving step d') is performed by dissolving the concentrate in a non-aromatic organic solvent. Suitable non-aromatic organic solvents include, but are not limited to, ethyl acetate, diethyl ether, methylene chloride, and mixtures thereof Preferably, the non-aromatic organic solvent is ethyl acetate.

Each of the above-described embodiments concludes with three steps: an extracting step; followed by an acidifying step; and then a collecting step.

In each embodiment, the extracting step a'), c'), or e') is performed by extracting the 1-methoxymethyl-5,5-diphenylbarbituric acid that is prepared in reacting step (a) from an organic solvent into a basic aqueous solution. Suitable organic solvents for the extracting step include, but are not limited to, aromatic solvents and non-aromatic organic solvents. Suitable aromatic solvents include, but are not limited to, chlorobenzene, bromobenzene, nitrobenzene, dichlorobenzene, o-nitrotoluene, anisole, and the like. Suitable non-aromatic organic solvents include, but are not limited to, ethyl acetate, methylene chloride, diethyl ether, and the like. Optionally, the organic solvent may include the reaction solvent.

The basic aqueous solution used in the extracting step may be prepared using any suitable method. Suitable methods include, but are not limited to, dissolving a base in water, and dissolving a base in a mixture of water and one or more water miscible organic solvents. Suitable bases include, but are not limited to, sodium hydroxide, potassium hydroxide, sodium carbonate, and potassium carbonate. Preferably, the base is sodium hydroxide. Suitable water miscible organic solvents include, but are not limited to, methanol.

In each embodiment, the acidifying step b'), d'), or f') is performed by reducing the pH of the basic aqueous solution enough to cause the 1-methoxymethyl-5,5-diphenylbarbituric acid to precipitate from solution. Suitable methods for performing the acidifying step include, but are not limited to, adding acid to the basic aqueous solution. Suitable acids include, but are not limited to, mineral acids. Mineral acids include, but are not limited to, hydrochloric acid, sulfuric acid, nitric acid, phosphoric acid, mixtures thereof and the like. Preferably, the pH of the solution is reduced to about 5 or lower. More preferably, the pH of the solution is reduced to about 4 or lower.

In each embodiment, the collecting step c'), e'), or g') may be performed using any suitable method. Suitable methods for collecting the precipitated 1-methoxymethyl-5,5-diphenylbarbituric acid include, but are not limited to, filtering, centrifuging, and decanting.

The isolated 1-methoxymethyl-5,5-diphenylbarbituric acid may be further purified. Suitable purification methods include, but are not limited to, high performance liquid chromatography (HPLC) and crystallization. Preferably, the isolated 1-methoxymethyl-5,5-diphenylbarbituric acid is purified by crystallization from a solvent. Suitable crystallization solvents include, but are not limited to, toluene, tert-butyl methyl ether, ethanol, methanol, water mixed with ethanol, and water mixed with methanol.

Preferably, the 1-methoxymethyl-5,5-diphenylbarbituric acid has a purity greater than 97%. More preferably, the 1-methoxymethyl-5,5-diphenylbarbituric acid has a purity greater than 98%. More preferably, the 1-methoxymethyl-5,5-diphenylbarbituric acid has a purity greater than 99%.

The present invention provides a process for preparing 1-methoxymethyl-5,5-diphenylbarbituric acid by removing one methoxymethyl group from 1,3-bis(methoxymethyl)-5,5-diphenylbarbituric acid. The present invention is further illustrated, but not limited, by the following examples.

EXAMPLES

Example 1

Preparation of 1-methoxymethyl-5,5-diphenylbarbituric acid

Reaction of 1,3-bis methoxymethyl)-5,5-diphenylbarbituric acid with a Lewis acid A reactor was charged with chlorobenzene (15 mL) under nitrogen with stirring. 1,3-bis(methoxymethyl)-5,5-diphenylbarbituric acid (1.84 g, 5 mmol) was added to the reactor, and the mixture was stirred for 10 minutes. The mixture was then heated to 55–60° C. and stirred for another 10 minutes. Aluminum chloride ($AlCl_3$, 0.66 g, 5 mmol, 1 equivalent) was added, and the mixture was stirred for 10 minutes at about 60° C. The mixture was then heated to 100–110° C. and stirred for another 10 minutes. The mixture was then cooled to about 60° C., and the nitrogen flow was stopped.

Isolation of 1-methoxymethyl-5,5-diphenylbarbituric acid

A cold solution of hydrochloric acid (32%, 0.5 mL) in deionized water (30 mL) was added to the mixture, and the resulting mixture was stirred at 5° C. for about 30 minutes. The resulting suspension was filtered, and the precipitate was washed with cold chlorobenzene (2 mL). The filtrates were combined, and the chlorobenzene (lower) phase was separated. A majority of the chlorobenzene phase was then removed by evaporation.

Ethyl acetate (10 mL) was added to the resulting concentrate, and the solution was extracted with 0.5 N sodium hydroxide (15 mL), while maintaining the solution at a temperature of 20° C. or lower. The phases were separated, and the ethyl acetate phase was washed with cold deionized water (15 mL). The phases were again separated, and the aqueous phases were combined. The combined aqueous phases were acidified with hydrochloric acid (32%, 1 mL), while maintaining the mixture at a temperature below 20° C., and the mixture was stirred for 30 minutes. The resulting suspension was then filtered, and the precipitate was washed with deionized water (5 mL) to yield crude 1-methoxymethyl-5,5-diphenylbarbituric acid (0.87 g).

Purification of 1-methoxymethyl-5,5-diphenylbarbituric acid

Ethanol (95%, 4.5 mL) was added to the crude 1-methoxymethyl-5,5-diphenylbarbituric acid. The resulting mixture was heated to 60° C. and stirred for about 30 minutes, then cooled to room temperature and stirred for an additional 30 minutes. The resulting suspension was filtered, and the precipitate was washed with ethanol (95%, 1 mL). The wet precipitate was dried in a vacuum oven at 60° C. for about 10 hours to provide 1-methoxymethyl-5,5-diphenylbarbituric acid. Yield: 26%; Purity: 98%

Example 2

Preparation of 1-methoxymethyl-5,5-diphenylbarbituric acid

Reaction of 1,3-bis(methoxymethyl)-5,5-diphenylbarbituric acid with a Lewis acid 1,3-bis(methoxymethyl)-5,5-diphenylbarbituric acid (1.04 kg, 2.82 mol) was suspended in chlorobenzene (8 L). The suspension was heated to 55–60° C. and stirred under nitrogen during 10 minutes. Aluminum chloride ($AlCl_3$, 0.23 kg, 1.73 mol, 0.6 equivalent) was then added in portions, and the suspension mixed at 55–60° C. for 30 minutes. The reaction mixture was then heated to 105° C. and stirred for 2–3 hours until complete dissolution was observed.

Isolation of 1-methoxymethyl-5,5-diphenylbarbituric acid

The reaction mixture was then cooled to 70–80° C. and water (4 L) was added. The resulting mixture was cooled to 10° C. and stirred for 10–21 hours. The resulting suspension was filtered, and the filtrate was separated into organic and aqueous phases. To the organic phase was added an aqueous solution of sodium hydroxide (50%, 0.23 kg), water (1.2 L), and methanol (5.7 L), the addition being performed at a temperature of 10° C. or lower. The two-phase mixture was then stirred for about 10 minutes, and the phases were separated.

To the aqueous phase was added hydrochloric acid (32%, 0.32 L), while keeping the temperature below 20° C. The methanol was then distilled out of the mixture at reduced pressure, and the resulting precipitate was filtered and dried to provide a crude product (0.366 kg) containing 1-methoxymethyl-5,5-diphenylbarbituric acid (78% w/w), 5,5-diphenylbarbituric acid (6% w/w), and 1,3-bis(methoxymethyl)-5,5-diphenylbarbituric acid (2.7% w/w).

Purification of 1-methoxymethyl-5,5-diphenylbarbituric acid

The crude product was combined with a mixture of methanol:water (1:1 (v/v), 10 L). The resulting mixture was heated to 70–75° C. and stirred for about 90 minutes, then cooled to room temperature and stirred for 30 minutes. The resulting precipitate was then filtered, washed with methanol:water (1:1 (v/v), about 1 L), and dried in a vacuum oven (60° C., about 10 hours) to provide a purified product (0.254 kg) containing 1-methoxymethyl-5,5-diphenylbarbituric acid (82% w/w), 5,5-diphenylbarbituric acid (4.2% w/w), and 1,3-bis(methoxymethyl)-5,5-diphenylbarbituric acid (1.7% w/w). In some experiments, this product was further recrystallized from toluene and then methanol to obtain 1-methoxymethyl-5,5-diphenylbarbituric acid having a purity of >99%.

All references cited herein are incorporated by reference. The embodiments illustrated and discussed in this specification are intended only to teach those skilled in the art to make and use the invention. Nothing in this specification should be considered as limiting the scope of the present invention. Modifications and variations of the above-described embodiments of the invention are possible without departing from the invention) as appreciated by those skilled in the art in light of the present teachings.

What is claimed is:

1. A process for preparing 1-methoxymethyl-5,5-diphenylbarbituric acid comprising the steps of
   (a) reacting 1,3-bis(methoxymethyl)-5,5-diphenylbarbituric acid with about 0.6 equivalent to about 1 equivalent of aluminum chloride, at a temperature of about 70° C. to about 130° C., for about two to about three hours; and
   (b) isolating the 1-methoxymethyl-5,5-diphenylbarbituric acid.

2. The process of claim 1, wherein step (a) is performed in chlorobenzene.

3. The process of claim 1, wherein step (b) further comprises the steps of:
   a') extracting the 1-methoxymethyl-5,5-diphenylbarbituric acid into an aqueous sodium hydroxide solution;
   b') acidifying the basic aqueous solution to precipitate the extracted 1-methoxymethyl-5,5-diphenylbarbituric acid; and
   c') collecting the precipitated 1-methoxymethyl-5,5-diphenylbarbituric acid.

4. The process of claim 1, further comprising the step of purifying the isolated 1-methoxymethyl-5,5-diphenylbarbituric acid.

5. The process of claim 4, wherein the purifying step is performed by crystallization from ethanol.

6. The process of claim 4, wherein the purifying step is performed by crystallization from a mixture of methanol and water.

7. The process of claim 6, wherein the purifying step further comprises recrystallization from toluene followed by methanol.

8. The process of claim 5, wherein the 1-methoxymethyl-5,5-diphenylbarbituric acid has a purity greater than 98%.

9. The process of claim 7, wherein the 1-methoxymethyl-5,5-diphenylbarbituric acid has a purity greater than 99%.

* * * * *